(12) United States Patent
Ito et al.

(10) Patent No.: US 8,481,753 B2
(45) Date of Patent: Jul. 9, 2013

(54) METHOD FOR PRODUCING ISOINDOLE

(75) Inventors: Satoshi Ito, Utsunomiya (JP); Naotsugu Itoh, Utsunomiya (JP); Takafumi Sato, Utsunomiya (JP)

(73) Assignee: Utsunomiya University, Utsunomiya-shi, Toshigi (JP)

( * ) Notice: Subject to any disclaimer, the term of this patent is extended or adjusted under 35 U.S.C. 154(b) by 155 days.

(21) Appl. No.: 12/864,618

(22) PCT Filed: Dec. 24, 2008

(86) PCT No.: PCT/JP2008/073392
§ 371 (c)(1),
(2), (4) Date: Oct. 13, 2010

(87) PCT Pub. No.: WO2009/096126
PCT Pub. Date: Aug. 6, 2009

(65) Prior Publication Data
US 2011/0137024 A1    Jun. 9, 2011

(30) Foreign Application Priority Data
Jan. 31, 2008 (JP) .................. 2008-020310

(51) Int. Cl.
*C07D 209/44* (2006.01)
(52) U.S. Cl.
USPC ...................................... 548/470
(58) Field of Classification Search
USPC ...................................... 548/470
See application file for complete search history.

(56) References Cited

PUBLICATIONS

Hidemitsu Uno et al. "Synthesis and Structures of Pyrroles Fused With Rigid Bicyclic Ring Systems at β-positions," *Journal of Chemical Society*, Perkin Trans. 1, 2000, pp. 4347-4355.
Satoshi Ito et al. "A New Synthesis of Benzoporphyrins Using 4,7-Dihydro-4, 7-Ethano-2*H*-Isoindole As An Isoindole Equivalent," *Heterocycles*, vol. 52, No. 1, 2000, pp. 399-411.
Hidemitsu Uno et al. "Soluble Precursors Convertible to Tetrabenzoporphyrins Below Room Temperature," *Tetrahedron Letters*, vol. 44, No. 28, 2003, pp. 5163-5165.
Mitsuo Wada et al. "Synthesis and Optical Properties of a New Class of Pyrromethene-BF$_2$ Complexes Fused With Rigid Bicyclo Rings and Benzo Derivatives," *Tetrahedron Letters*, vol. 42, No. 38, 2001, pp. 6711-6713.
R. Scott Oakes et al. "The Use of Supercritical Fluids in Synthetic Organic Chemistry," *Journal of Chemical Society*, Perkin Trans. 1, No. 9, 2001, pp. 917-941.
Vladimir V. Kouznetsov et al. "Three-component Imino Diels-Alder Reaction With Essential Oil and Seeds of Anise; Generation of New Tetrahydroquinolines," *Tetrahedron Letters*, vol. 48, No. 50, 2007, pp. 8855-8860.
R. Bonnett et al. "Isoindole," *Chemical Communications*, 1972, pp. 393-395.
J. Bornstein et al. "Synthesis of Isoindole by Retro-Diels-Alder Reaction," *Chemical Communications*, 1972, pp. 1149-1150.
Ito, Satoshi et al., "A New Synthesis of Benzoporphyrins Using 4,7-dihydro-4,7-ethano-2*H*-isoindole as a Synthon of Isoindole," Chemical Communications(Cambridge), (16), 1661-1662 CODEN: CHCOFS; ISSN:1359-7345, 1998, XP002475055.

*Primary Examiner* — Brian McDowell
(74) *Attorney, Agent, or Firm* — Drinker Biddle & Reath LLP

(57) ABSTRACT

A method for manufacturing isoindolic compound, which can adopt a condition capable of being put to industrially practical use, which can produce stable isoindolic compound, and which can further produce the isoindolic compound with a high yield. The method for manufacturing isoindolic compound includes a thermal treatment step where a compound of which molecule includes a structure of pyrrole fused with bicyclo [2.2.2] octadiene skeleton, and includes a formula (I):

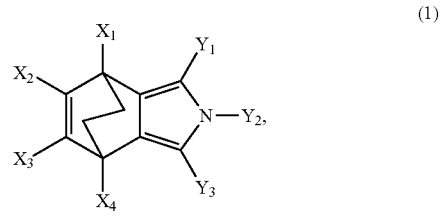

(1)

is subjected to a supercritical carbon dioxide atmosphere. The thermal treatment step is preferably performed at a temperature of not less than 50° C. and not more than 300° C.

2 Claims, No Drawings

METHOD FOR PRODUCING ISOINDOLE

TECHNICAL FIELD

This invention is related to a method for manufacturing isoindolic compound and isoindolic compound manufactured thereby.

BACKGROUND ART

The isoindole has been used, for instance, as a fluorescent labeling reagent, an antihypertensive agent, and a physiologically active substance, and it is known that the non-substituted form of the isoindole tends to decompose readily in air at the room temperature. Although such an isoindole has been utilized for the above mentioned uses even in its as-is form and its derivative form, polymer forms of the isoindole, i.e., pyrromethene has been used as a red organic EL (electroluminescence) material, and tetrabenzoporphyrin and phthalocyanine have been used as organic semiconductor, photosensitizer for photo dynamic therapy of cancer, solar cell material, and pigment, etc.

Non-patent literatures 1-3 can be enumerated as literatures which disclose the method of manufacturing the isoindole. Concretely, in the non-patent literatures 1 and 2, the condition of 500° C./0.01 mmHg or 600° C., and in the non-patent literature 3, the thermal decomposition condition of 230° C. with using diphenyl ether, are used respectively.

Non-patent literature 1: R. Bonnett and R. F. C. Brown, "Isoindole" Chem. Commun., 393-395, 1972

Non-patent literature 2: J. Bornstein, D. E. Remy and J. E. Shields, "Synthesis of isoindole by retro-Diels-Alder reaction" Chem. Commun., 1149-1150, 1972

Non-patent literature 3: H. Uno, S. Ito, M. Wada, H. Watanabe, M. Nagai, A. Hayashi, T. Murashima and N. Ono, "Synthesis and structures of pyrroles fused with rigid bicyclic ring systems at β-positions" J. Chem. Soc., Perkin Trans. 1, 4347-4355, 2000

DISCLOSURE OF THE INVENTION

Problem to be Solved by the Invention

However, the condition of 500° C./0.01 mmHg or 600° C. disclosed by the non-patent literatures 1 and 2 is very severe one as the temperature and pressure conditions for organic synthesis, and therefore, a problem that the practical use of the method is difficult arises from the viewpoint of industrialization. Additionally, since the synthesized isoindoles are non-substituted ones, there is a problem that they are not stable and they are readily decomposed in air at the room temperature.

In the non-patent documents 3, the method is used where an isoindole derivative is obtained by using diphenyl ether as a solvent, and decomposing thermally a compound, of which molecule includes a structure of pyrrole fused with bicyclo [2.2.2] octadiene skeleton, in the solvent. That is because the diphenyl ether is a solvent having a high boiling point, thus it is thermally stable and it is hardly volatile, and therefore, it is possible to make the deairation in the reaction system easy. However, according to our investigation, it was found that it is difficult to remove oxygen completely from the reaction system. Further, the diphenyl ether per se is an ether compound. Owing to these facts, oxygen and/or peroxide generates and/or remains in the reaction system. Thereby, other compounds such as phthalimide are inevitably synthesized, and the yield of the isoindole does not reach 15%, or it is of the order, at most, of about 33%. Thus, the manufacturing method disclosed in the non-patent literature 3 remains a problem about the yield of the isoindole.

The present invention has been contrived in order to solve the above mentioned problems, and firstly, the present invention is aimed to provide a method for manufacturing isoindolic compound, which can adopt a condition capable of being put to industrially practical use, which can produce stable isoindolic compound, and which can further produce the isoindolic compound with a high yield.

The present invention has been contrived in order to solve the above mentioned problems, and secondary, the present invention is aimed to provide isoindolic compound, which is manufactured by the method for manufacturing isoindolic compound, which can adopt a condition capable of being put to industrially practical use, which can produce stable isoindolic compound, and which can further produce the isoindolic compound with a high yield.

Means for Solving the Problem

Under such purposes, we have made diligent study and investigation. As a result, we have found that isoindolic compound can be produced with a high yield under a condition capable of being put to industrially practical use, by subjecting a compound of which molecule includes a structure of pyrrole fused with bicyclo [2.2.2] octadiene skeleton to a supercritical carbon dioxide atmosphere, and then we have completed the present invention.

The method for manufacturing isoindolic compound of the present invention to solve the above mentioned problem is characterized in having a thermal treatment step where a compound of which molecule includes a structure of pyrrole fused with bicyclo [2.2.2] octadiene skeleton is subjected to a supercritical carbon dioxide atmosphere.

According to the present invention, since the method comprises the thermal treatment step where the compound of which molecule includes the structure of pyrrole fused with bicyclo [2.2.2] octadiene skeleton is subjected to the supercritical carbon dioxide atmosphere, the deairation in the reaction system can be progressed satisfactorily by means of the supercritical carbon dioxide atmosphere, and the compound of which molecule includes the structure of pyrrole fused with bicyclo [2.2.2] octadiene skeleton as a raw material can be dispersed and/or solved satisfactorily. Thus, it is possible to perform the thermal treatment efficiently. As a consequence, the reaction can progress at a relatively low temperature, and therefore, it becomes possible to provide a method for manufacturing isoindolic compound which can employ a condition capable of being put to industrially practical use, can produce stable isoindolic compound, and can further produce the isoindolic compound with a high yield.

In a preferable embodiment of the method for manufacturing isoindolic compound according to the present invention, the above mentioned thermal treatment step is performed at a temperature of not less than 50° C. and not more than 300° C.

According to this embodiment of the present invention, since the thermal treatment step is performed at a temperature of not less than 50° C. and not more than 300° C., the thermal treatment in a desirable range of the temperature is accomplished. As a result, it is possible to produce the isoindolic compound more efficiently.

In a preferable embodiment of the method for manufacturing isoindolic compound according to the present invention, the above mentioned compound of which molecule includes the structure of pyrrole fused with bicyclo [2.2.2] octadiene skeleton is represented by the following general formula (1):

[Chemical 1]

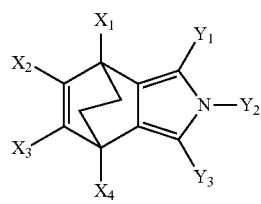
(1)

(In the general formula (1), $Y_1$ and $Y_3$ mutually independently represent hydrogen, linear- or branched-alkyl group having a carbon number of 1-18, cyclic alkyl group having a carbon number of 3-18, linear- or branched-alkenyl group having a carbon number of 2-18, cyclic alkenyl group having a carbon number of 3-18, aralkyl group having a carbon number of 7-20, aryl group having a carbon number of 6-18, halogen atom, nitro group, nitroso group, cyano group, isocyano group, cyanato group, isocyanato group, thiocyanato group, isothiocyanato group, mercapto group, hydroxy group, hydroxyamino group, formyl group, sulfo group, carboxyl group, acyl group, amino group, acylamino group, carbamate group, carboxylate group, acyloxy group, carbamoyl group, sulfonyl group, sulfamoyl group, sulfonate group, sulfonamide group, sulfinyl group, or heterocyclic group;

$Y_2$ represents hydrogen, linear- or branched-alkyl group having a carbon number of 1-18, cyclic alkyl group having a carbon number of 3-18, linear- or branched-alkenyl group having a carbon number of 2-18, cyclic alkenyl group having a carbon number of 3-18, aralkyl group having a carbon number of 7-20, aryl group having a carbon number of 6-18, formyl group, sulfo group, carboxyl group, acyl group, carboxylate group, acyloxy group, carbamoyl group, sulfonyl group, sulfamoyl group, silyl group, or heterocyclic group;

$X_1$-$X_4$ mutually independently represent hydrogen, linear- or branched-alkyl group having a carbon number of 1-18, cyclic alkyl group having a carbon number of 3-18, linear- or branched-alkenyl group having a carbon number of 2-18, cyclic alkenyl group having a carbon number of 3-18, aralkyl group having a carbon number of 7-20, aryl group having a carbon number of 6-18, halogen atom, nitro group, nitroso group, cyano group, isocyano group, cyanato group, isocyanato group, thiocyanato group, isothiocyanato group, mercapto group, hydroxy group, hydroxyamino group, formyl group, sulfo group, carboxyl group, acyl group, amino group, acylamino group, carbamate group, carboxylate group, acyloxy group, carbamoyl group, sulfonyl group, sulfamoyl group, sulfonate group, sulfonamide group, or sulfinyl group; wherein $X_2$ and $X_3$ may be optionally linked together to form a ring structure.)

According to this embodiment of the present invention, since the compounds represented by the general formula (1) are used as the compound of which molecule includes the structure of pyrrole fused with bicyclo [2.2.2] octadiene skeleton, it becomes possible to use various compounds each of which molecule includes one structure of pyrrole fused with bicyclo [2.2.2] octadiene skeleton, and as a result, it becomes possible to obtain various isoindole derivatives.

In a preferable embodiment of the method for manufacturing isoindolic compound according to the present invention, the above mentioned compound of which molecule includes the structure of pyrrole fused with bicyclo [2.2.2] octadiene skeleton is represented by the following general formula (2):

[Chemical 2]

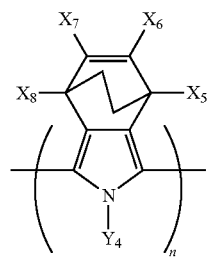
(2)

(In the general formula (2), n represents an integer of more than 1;

$Y_4$ represents hydrogen, linear- or branched-alkyl group having a carbon number of 1-18, cyclic alkyl group having a carbon number of 3-18, linear- or branched-alkenyl group having a carbon number of 2-18, cyclic alkenyl group having a carbon number of 3-18, aralkyl group having a carbon number of 7-20, aryl group having a carbon number of 6-18, formyl group, sulfo group, carboxyl group, acyl group, carboxylate group, acyloxy group, carbamoyl group, sulfonyl group, sulfamoyl group, silyl group, or heterocyclic group;

$X_5$-$X_8$ mutually independently represent hydrogen, linear- or branched-alkyl group having a carbon number of 1-18, cyclic alkyl group having a carbon number of 3-18, linear- or branched-alkenyl group having a carbon number of 2-18, cyclic alkenyl group having a carbon number of 3-18, aralkyl group having a carbon number of 7-20, aryl group having a carbon number of 6-18, halogen atom, nitro group, nitroso group, cyano group, isocyano group, cyanato group, isocyanato group, thiocyanato group, isothiocyanato group, mercapto group, hydroxy group, hydroxyamino group, formyl group, sulfo group, carboxyl group, acyl group, amino group, acylamino group, carbamate group, carboxylate group, acyloxy group, carbamoyl group, sulfonyl group, sulfamoyl group, sulfonate group, sulfonamide group, or sulfinyl group; wherein $X_6$ and $X_7$ may be optionally linked together to form a ring structure.)

According to this embodiment of the present invention, since the compounds represented by the general formula (2) are used as the compound of which molecule includes the structure of pyrrole fused with bicyclo [2.2.2] octadiene skeleton, it becomes possible to use various polymer compounds each of which molecule includes two or more of the structures of pyrroles fused with bicyclo [2.2.2] octadiene skeletons, and as a result, it becomes possible to obtain various polyisoindole derivatives.

In a preferable embodiment of the method for manufacturing isoindolic compound according to the present invention, the above mentioned compound of which molecule includes the structure of pyrrole fused with bicyclo [2.2.2] octadiene skeleton is represented by the following general formulae (3A) or (3B):

[Chemical 3]

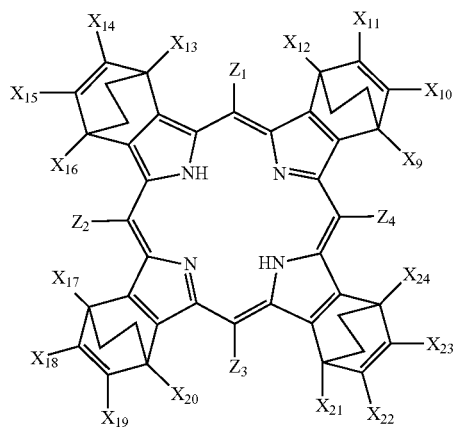
(3A)

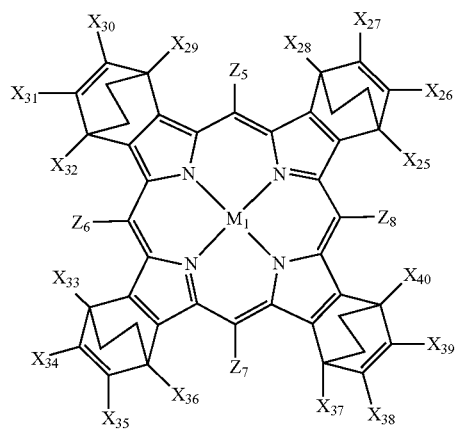
(3B)

(In the general formula (3A) and the general formula (3B), $Z_1$-$Z_8$ mutually independently represent hydrogen, linear- or branched-alkyl group having a carbon number of 1-18, cyclic alkyl group having a carbon number of 3-18, linear- or branched-alkenyl group having a carbon number of 2-18, cyclic alkenyl group having a carbon number of 3-18, aralkyl group having a carbon number of 7-20, aryl group having a carbon number of 6-18, halogen atom, nitro group, nitroso group, cyano group, isocyano group, cyanato group, isocyanato group, thiocyanato group, isothiocyariato group, mercapto group, hydroxy group, hydroxyamino group, formyl group, sulfo group, carboxyl group, acyl group, amino group, acylamino group, carbamate group, carboxylate group, acyloxy group, or carbamoyl group;

$X_9$-$X_{40}$ mutually independently represent hydrogen, linear- or branched-alkyl group having a carbon number of 1-18, cyclic alkyl group having a carbon number of 3-18, linear- or branched-alkenyl group having a carbon number of 2-18, cyclic alkenyl group having a carbon number of 3-18, aralkyl group having a carbon number of 7-20, aryl group having a carbon number of 6-18, halogen atom, nitro group, nitroso group, cyano group, isocyano group, cyanato group, isocyanato group, thiocyanato group, isothiocyanato group, mercapto group, hydroxy group, hydroxyamino group, formyl group, sulfo group, carboxyl group, acyl group, amino group, acylamino group, carbamate group, carboxylate group, acyloxy group, carbamoyl group, sulfonyl group, sulfamoyl group, sulfonate group, sulfonamide group, or sulfinyl group; wherein $X_{10}$ and $X_{11}$, $X_{14}$ and $X_{15}$, $X_{18}$ and $X_{19}$, $X_{22}$ and $X_{23}$, $X_{26}$ and $X_{27}$, $X_{30}$ and $X_{31}$, $X_{34}$ and $X_{35}$, and $X_{38}$ and $X_{39}$ may be optionally linked together, respectively, to form their individual ring structures; and $M_1$ represents a metal atom.)

According to this embodiment of the present invention, since the compounds represented by the general formula (3A) and the general formula (3B) are used as the compound of which molecule includes the structure of pyrrole fused with bicyclo [2.2.2] octadiene skeleton, it becomes possible to use a variety of bicycloporphyrins, and as a result, it becomes possible to obtain various tetrabenzoporphyrins.

In a preferable embodiment of the method for manufacturing isoindolic compound according to the present invention, the above mentioned compound of which molecule includes the structure of pyrrole fused with bicyclo [2.2.2] octadiene skeleton is represented by the following general formula (4):

[Chemical 4]

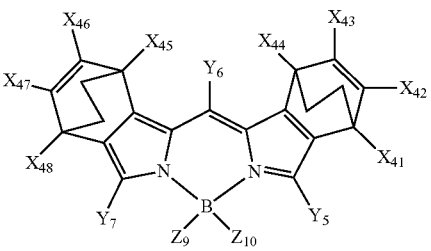
(4)

(In the general formula (4), $Y_5$ and $Y_7$ mutually independently represent hydrogen, linear- or branched-alkyl group having a carbon number of 1-18, cyclic alkyl group having a carbon number of 3-18, linear- or branched-alkenyl group having a carbon number of 2-18, cyclic alkenyl group having a carbon number of 3-18, aralkyl group having a carbon number of 7-20, aryl group having a carbon number of 6-18, halogen atom, nitro group, nitroso group, cyano group, isocyano group, cyanato group, isocyanato group, thiocyanato group, isothiocyanato group, mercapto group, hydroxy group, hydroxyamino group, formyl group, sulfo group, carboxyl group, acyl group, amino group, acylamino group, carbamate group, carboxylate group, acyloxy group, carbamoyl group, sulfonyl group, sulfamoyl group, sulfonate group, sulfonamide group, sulfinyl group or heterocyclic group;

$Y_6$ represents hydrogen, linear- or branched-alkyl group having a carbon number of 1-18, cyclic alkyl group having a carbon number of 3-18, linear- or branched-alkenyl group having a carbon number of 2-18, cyclic alkenyl group having a carbon number of 3-18, aralkyl group having a carbon number of 7-20, aryl group having a carbon number of 6-18, or heterocyclic group;

$Z_9$ and $Z_{10}$ mutually independently represent hydrogen, linear- or branched-alkyl group having a carbon number of 1-18, aryl group having a carbon number of 6-18, halogen atom, or a monovalent group of pyrrole fused with bicyclo [2.2.2] octadiene skeleton or derivative thereof;

$X_{41}$-$X_{48}$ mutually independently represent hydrogen, linear- or branched-alkyl group having a carbon number of 1-18, cyclic alkyl group having a carbon number of 3-18, linear- or branched-alkenyl group having a carbon number of 2-18, cyclic alkenyl group having a carbon number of 3-18, aralkyl group having a carbon number of 7-20, aryl group having a carbon number of 6-18, halogen atom, nitro group, nitroso group, cyano group, isocyano group, cyanato group, isocyanato group, thiocyanato group, isothiocyanato group, mercapto group, hydroxy group, hydroxyamino group, formyl group, sulfo group, carboxyl group, acyl group, amino group, acylamino group, carbamate group, carboxylate group, acyloxy group, carbamoyl group, sulfonyl group, sulfamoyl group, sulfonate group, sulfonamide group, or sulfinyl group; wherein $X_{42}$ and $X_{43}$, and $X_{46}$ and $X_{47}$ may be optionally linked together, respectively, to form their individual ring structures.)

According to this embodiment of the present invention, since the compounds represented by the general formula (4) are used as the compound of which molecule includes the structure of pyrrole fused with bicyclo [2.2.2] octadiene skeleton, it becomes possible to use a variety of pyrromethenes, and as a result, it becomes possible to obtain various benzopyrromethenes.

Isoindolic compound of the present invention to solve the above mentioned problem is characterized in being obtained by the above mentioned method for manufacturing isoindolic compound.

According to this invention, since the isoindolic compound is obtained by the above mentioned method for manufacturing isoindolic compound, it is possible to provide the isoindolic compound which is obtained by the method for manufacturing isoindolic compound where the deairation in the reaction system can be progressed satisfactorily by means of the supercritical carbon dioxide atmosphere, and the compound of which molecule includes a structure of pyrrole fused with bicycle [2.2.2] octadiene skeleton as a raw material can be dispersed and/or solved satisfactorily, which is followed by the implementation of an efficient thermal treatment, and thus the progress of the reaction at a relatively low temperature, the capability of applying a condition capable of being put to industrially practical use, the ability of producing stable isoindolic compound, and the ability of producing the isoindolic compound with a high yield.

Effect of Invention

According to the method for manufacturing isoindolic compound of the present invention, it is possible to provide a method for manufacturing isoindolic compound which can employ a condition capable of being put to industrially practical use, can produce stable isoindolic compound, and can further produce the isoindolic compound with a high yield.

Since the isoindolic compound according to the present invention is obtained by the method for manufacturing isoindolic compound which can employ a condition capable of being put to industrially practical use, can produce stable isoindolic compound, and can further produce the isoindolic compound with a high yield, it is possible to provide stable isoindolic compound with a high purity.

BEST MODE FOR CARRYING OUT THE INVENTION

Now, some embodiments of the present invention will be described in detail. However, the present invention is not limited to the following embodiments, and the present invention can be carried out by making a variety of variations or modifications within the scope and spirit of the present invention.

The method for manufacturing isoindolic compound according to the present invention comprises a thermal treatment step where a compound of which molecule includes a structure of pyrrole fused with bicyclo [2.2.2] octadiene skeleton is subjected to a supercritical carbon dioxide atmosphere. By applying the supercritical carbon dioxide atmosphere, the deairation in the reaction system can be progressed satisfactorily, and the compound of which molecule includes the structure of pyrrole fused with bicyclo [2.2.2] octadiene skeleton as a raw material can be dispersed and/or solved satisfactorily. Thus, it is possible to perform the thermal treatment efficiently. As a consequence, the reaction can progress at a relatively low temperature, and therefore, it becomes possible to provide a method for manufacturing isoindolic compound which can employ a condition capable of being put to industrially practical use, can produce stable isoindolic compound, and can further produce the isoindolic compound with a high yield.

Herein, the "compound of which molecule includes a structure of pyrrole fused with bicyclo [2.2.2] octadiene skeleton" denotes, as its name implies, compound which has at least one structure of pyrrole fused with bicyclo [2.2.2] octadiene skeleton, i.e., a structure where a bicyclo [2.2.2] octadiene skeleton and a pyrrole ring are fused together with a common edge, in its molecule. In the present invention, the reaction of converting the bicyclo [2.2.2] octadiene skeleton into a benzene skeleton is accelerated by subjecting the compound under the supercritical carbon dioxide atmosphere while the compound undergoes the thermal treatment. As a result, the isoindolic compound of which molecule includes at least one isoindole structure can be obtained with high yields. Incidentally, hereinafter, the "compound of which molecule includes a structure of pyrrole fused with bicyclo [2.2.2] octadiene skeleton" may be sometimes abbreviated as "compound of which molecule includes a structure of bicyclopyrrole" and the "structure of pyrrole fused with bicyclo [2.2.2] octadiene skeleton" may be sometimes abbreviated as "structure of bicyclopyrrole", for the sake of convenience.

As the compound of which molecule includes a structure of pyrrole fused with bicyclo [2.2.2] octadiene skeleton, monomers each of which has a single structure of bicyclopyrrole, and polymers each of which has two or more of the structures of bicyclopyrroles may be exemplified. Although the following are explained about some preferred enumerations, it will be understood that there is no particular limitation about the compound, and thus the compound is not limited to the following enumerations.

(Monomeric Compound of which Molecule Includes a Structure of Bicyclopyrrole)

When a monomeric compound of which molecule includes a structure of bicyclopyrrole is used, it is desirable to use the compound represented by the following general formula (1).

[Chemical 5]

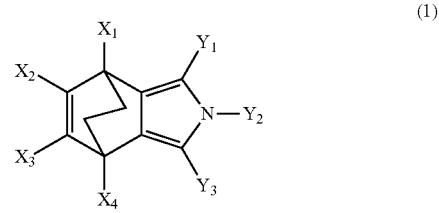

(1)

(In the general formula (1), $Y_1$ and $Y_3$ mutually independently represent hydrogen, linear- or branched-alkyl group having a carbon number of 1-18, cyclic alkyl group having a carbon number of 3-18, linear- or branched-alkenyl group having a carbon number of 2-18, cyclic alkenyl group having a carbon number of 3-18, aralkyl group having a carbon number of 7-20, aryl group having a carbon number of 6-18, halogen atom, nitro group, nitroso group, cyano group, isocyano group, cyanato group, isocyanato group, thiocyanato group, isothiocyanato group, mercapto group, hydroxy group, hydroxyamino group, formyl group, sulfo group, carboxyl group, acyl group, amino group, acylamino group, carbamate group, carboxylate group, acyloxy group, carbamoyl group, sulfonyl group, sulfamoyl group, sulfonate group, sulfonamide group, sulfinyl group, or heterocyclic group;

$Y_2$ represents hydrogen, linear- or branched-alkyl group having a carbon number of 1-18, cyclic alkyl group having a carbon number of 3-18, linear- or branched-alkenyl group having a carbon number of 2-18, cyclic alkenyl group having a carbon number of 3-18, aralkyl group having a carbon number of 7-20, aryl group having a carbon number of 6-18, formyl group, sulfo group, carboxyl group, acyl group, carboxylate group, acyloxy group, carbamoyl group, sulfonyl group, sulfamoyl group, silyl group, or heterocyclic group;

$X_1$-$X_4$ mutually independently represent hydrogen, linear- or branched-alkyl group having a carbon number of 1-18, cyclic alkyl group having a carbon number of 3-18, linear- or branched-alkenyl group having a carbon number of 2-18, cyclic alkenyl group having a carbon number of 3-18, aralkyl group having a carbon number of 7-20, aryl group having a carbon number of 6-18, halogen atom, nitro group, nitroso group, cyano group, isocyano group, cyanato group, isocyanato group, thiocyanato group, isothiocyanato group, mercapto group, hydroxy group, hydroxyamino group, formyl group, sulfo group, carboxyl group, acyl group, amino group, acylamino group, carbamate group, carboxylate group, acyloxy group, carbamoyl group, sulfonyl group, sulfamoyl group, sulfonate group, sulfonamide group, or sulfinyl group; wherein $X_2$ and $X_3$ may be optionally linked together to form a ring structure.)

When adopting the compounds represented by the general formula (1), it becomes possible to use various compounds each of which molecule includes one bicyclopyrrole structure, and as a result, it becomes possible to obtain various isoindole derivatives.

In the general formula (1), $Y_1$ and $Y_3$ mutually independently represent hydrogen, linear- or branched-alkyl group having a carbon number of 1-18, cyclic alkyl group having a carbon number of 3-18, linear- or branched-alkenyl group having a carbon number of 2-18, cyclic alkenyl group having a carbon number of 3-18, aralkyl group having a carbon number of 7-20, aryl group having a carbon number of 6-18, halogen atom, nitro group, nitroso group, cyano group, isocyano group, cyanato group, isocyanato group, thiocyanato group, isothiocyanato group, mercapto group, hydroxy group, hydroxyamino group, formyl group, sulfo group, carboxyl group, acyl group, amino group, acylamino group, carbamate group, carboxylate group, acyloxy group, carbamoyl group, sulfonyl group, sulfamoyl group, sulfonate group, sulfonamide group, sulfinyl group, or heterocyclic group.

The following may be enumerated as the linear- or branched-alkyl group having a carbon number of 1-18, the cyclic alkyl group having a carbon number of 3-18, the linear- or branched-alkenyl group having a carbon number of 2-18, the cyclic alkenyl group having a carbon number of 3-18, the aralkyl group having a carbon number of 7-20, and the aryl group having a carbon number of 6-18, all of which can be used for $Y_1$ and $Y_3$. Namely, as the linear- or branched-alkyl group having a carbon number of 1-18, for instance, methyl group, ethyl group, propyl group, isopropyl group, n-butyl group, sec-butyl group, tert-butyl group, n-heptyl group, etc., may be enumerated. As the cyclic alkyl group having a carbon number of 3-18, for instance, cyclopropyl group, cyclopentyl group, cyclohexyl group, adamantyl group, etc., may be enumerated. As the linear- or branched-alkenyl group having a carbon number of 2-18, for instance, vinyl group, propenyl group, hexenyl group, etc., may be enumarated. As the cyclic alkenyl group having a carbon number of 3-18, for instance, cyclopentenyl group, cyclohexenyl group, etc., may be enumerated. As the aralkyl group having a carbon number of 7-20, for instance, benzyl group, phenethyl group, etc., may be enumerated. As the aryl group having a carbon number of 6-18, for instance, phenyl group, tolyl group, xylyl group, mesityl group, etc., may be enumerated. These organic groups may be further substituted by any of the substituents which are described later as those which may be possessed by R and R'.

As the halogen atom which can be used for $Y_1$ and $Y_3$, for instance, F, Cl, Br, and I may be enumerated.

The acyl group which can be used for $Y_1$ and $Y_3$ is usually represented by —COR, the amino group which can be used ditto is usually represented by —NRR', the acylamino group which can be used ditto is usually represented by —NHCOR, the carbamate group c which can be used ditto is usually represented by —NHCOOR, the carboxylate group which can be used ditto is usually represented by —COOR, the acyloxy group which can be used ditto is usually represented by —OCOR, the carbamoyl group which can be used ditto is usually represented by —CONRR', the sulfonyl group which can be used ditto is usually represented by —SO$_2$R, the sulfamoyl group which can be used ditto is usually represented by —SO$_2$NRR', the sulfonate group which can be used ditto is usually represented by —SO$_3$R, the sulfonamide group which can be used ditto is usually represented by —NHSO$_2$R, and the sulfinyl group which can be used ditto is usually represented by —SOR.

Herein, each of R and R' means an arbitrary substituent. Typically, hydrogen, halogen atom, or hydrocarbon group can be used for R and R' independently. However, for instance, in the case of the carboxylate group (—COOR), R is not hydrogen, because the carboxylate group is a ester group. It should be noted that this respect is applied in an analogous fashion on other substituents.

As the halogen atom which can be used for R and R', for instance, F, Cl, Br, and I may be enumerated.

As the hydrocarbon group which can be used for R and R', for instance, linear- or branched-alkyl groups; cyclic alkyl groups; linear- or branched-alkenyl groups; cyclic alkenyl groups; aralkyl groups; and aryl groups may be enumerated. Particularly, as the R and R', it is preferable to use linear- or branched-alkyl group having a carbon number of 1-18, such as methyl group, ethyl group, propyl group, isopropyl group, n-butyl group, sec-butyl group, tert-butyl group, n-heptyl group, etc.; cyclic alkyl group having a carbon number of 3-18, such as cyclopropyl group, cyclopentyl group, cyclohexyl group, adamantyl group, etc.; linear- or branched-alkenyl group having a carbon number of 2-18, such as vinyl group, propenyl group, hexenyl group, etc.; cyclic alkenyl group having a carbon number of 3-18, such as cyclopentenyl group, cyclohexenyl group, etc.; aralkyl group having a carbon number of 7-20, such as benzyl group, phenethyl group, etc.; or aryl group having a carbon number of 6-18, such as phenyl group, tolyl group, xylyl group, mesityl group, etc.

In addition, the aryl group moiety as R or R' may be optionally substituted by a further substituent. As such a substituent, for instance, alkoxy group having a carbon number of 1-10, such as methoxy group, ethoxy group, n-propoxy group, isopropoxy group, n-butoxy group, sec-butoxy group, tert-butoxy group, etc.; alkoxy alkoxy group having a carbon number of 2-12, such as methoxy methoxy group, ethoxy methoxy group, propoxy methoxy group, ethoxy ethoxy group, propoxy ethoxy group, methoxy butoxy group, etc.; alkoxy alkoxy alkoxy group having a carbon number of 3-15, such as methoxy methoxy methoxy group, methoxy methoxy ethoxy group, methoxy ethoxy methoxy group, methoxy ethoxy ethoxy group, ethoxy ethoxy methoxy group, etc.; aryl group having a carbon number of 6-12 (which may be optionally substituted by a further arbitrary substituent), such as, phenyl group, tolyl group, xylyl group, etc.; aryloxy group having a carbon number of 6-12, such as phenoxy group, tolyloxy group, xylyloxy group, naphtyloxy group, etc.; and alkenyloxy group having a carbon number of 2-12, such as allyloxy group, vinyloxy group, etc.; may be enumerated.

Further, as the other substituents, for instance, heterocyclic group, such as 2-thienyl group, 2-pyridyl group, 4-piperidyl group, morpholino group, etc.; cyano group; nitro group; hydroxyl group; alkyl amino group having a carbon number of 1-10, such as N,N-dimethyl amino group, N,N-diethyl amino group, etc.; alkyl sulfonyl amino group having a carbon number of 1-6, such as methyl sulfonyl amino group, ethyl sulfonyl amino group, n-propyl sulfonyl amino group, etc.; halogen atom, such as fluorine atom, chlorine atom, bromine atom, etc.; alkoxy carbonyl group having a carbon number of 2-7, such as carboxyl group, methoxy carbonyl group, ethoxy carbonyl group, n-propoxy carbonyl group, isopropoxy carbonyl group, n-butoxy carbonyl group, etc.; alkyl carbonyloxy group having a carbon number of 2-7, such as methyl carbonyloxy group, ethyl carbonyloxy group, n-propyl carbonyloxy group, isopropyl carbonyloxy group, n-butyl carbonyloxy group, etc.; alkoxy carbonyloxy group having a carbon number of 2-7, such as methoxy carbonyloxy group, ethoxy carbonyloxy group, n-propoxy carbonyloxy group, isopropoxy carbonyloxy group, n-butoxy carbonyloxy group, etc.; may be also enumerated.

With respect to the heterocyclic group which can be used for $Y_1$ and $Y_3$, it may be either a saturated heterocyclic group, such as 4-piperidyl group, morpholino group, 2-morpholinyl group, piperazyl groups, etc; or a aromatic heterocyclic group, such as 2-furyl group, 2-pyridyl group, 2-thiazolyl group, 2-quinolyl group, etc. The heterocyclic group may contain two or more number of heteroatoms, and may have additional substituent(s), optionally. Further, there is no particular limitation for the binding site thereof. As preferable structures for the heterocyclic ring, 5- and 6-membered saturated heterocyclic rings, 5- and 6-membered monocyclic hetero-aromatic rings, and dicyclic condensed hetero-aromatic rings each of which is formed by condensation of two of the monocyclic hetero-aromatic rings may be enumerated.

In the general formula (1), $Y_2$ represents hydrogen, linear- or branched-alkyl group having a carbon number of 1-18, cyclic alkyl group having a carbon number of 3-18, linear- or branched-alkenyl group having a carbon number of 2-18, cyclic alkenyl group having a carbon number of 3-18, aralkyl group having a carbon number of 7-20, aryl group having a carbon number of 6-18, formyl group, sulfo group, carboxyl group, acyl group, carboxylate group, acyloxy group, carbamoyl group, sulfonyl group, sulfamoyl group, silyl group, or heterocyclic group.

The following may be enumerated as the linear- or branched-alkyl group having a carbon number of 1-18, the cyclic alkyl group having a carbon number of 3-18, the linear- or branched-alkenyl group having a carbon number of 2-18, the cyclic alkenyl group having a carbon number of 3-18, the aralkyl group having a carbon number of 7-20, and the aryl group having a carbon number of 6-18, all of which can be used for $Y_2$. Namely, as the linear- or branched-alkyl group having a carbon number of 1-18, for instance, methyl group, ethyl group, propyl group, isopropyl group, n-butyl group, sec-butyl group, tert-butyl group, n-heptyl group, etc., may be enumerated. As the cyclic alkyl group having a carbon number of 3-18, for instance, cyclopropyl group, cyclopentyl group, cyclohexyl group, adamantyl group, etc., may be enumerated. As the linear- or branched-alkenyl group having a carbon number of 2-18, for instance, vinyl group, propenyl group, hexenyl group, etc., may be enumarated. As the cyclic alkenyl group having a carbon number of 3-18, for instance, cyclopentenyl group, cyclohexenyl group, etc., may be enumerated. As the aralkyl group having a carbon number of 7-20, for instance, benzyl group, phenethyl group, etc., may be enumerated. As the aryl group having a carbon number of 6-18, for instance, phenyl group, tolyl group, xylyl group, mesityl group, etc., may be enumerated.

The acyl group which can be used for $Y_2$ is usually represented by —COR, the carboxylate group which can be used ditto is usually represented by —COOR, the acyloxy group which can be used ditto is usually represented by —OCOR, the carbamoyl group which can be used ditto is usually represented by —CONRR', the sulfonyl group which can be used ditto is usually represented by —SO$_2$R, the sulfamoyl group which can be used ditto is usually represented by —SO$_2$NRR', and the silyl group which can be used ditto is usually represented by —SiRR'R". As for R, R', and R", similar substituents which are described above with respect to the former R and R' may be used, respectively.

With respect to the heterocyclic group which can be used for $Y_2$, it may be either a saturated heterocyclic group, such as 4-piperidyl group, morpholino group, 2-morpholinyl group, piperazyl groups, etc; or a aromatic heterocyclic group, such as 2-furyl group, 2-pyridyl group, 2-thiazolyl group, 2-quinolyl group, etc. The heterocyclic group may contain two or more number of heteroatoms, and may have additional substituent(s), optionally. Further, there is no particular limitation for the binding site thereof. As preferable structures for the heterocyclic ring, 5- and 6-membered saturated heterocyclic rings, 5- and 6-membered monocyclic hetero-aromatic rings, and dicyclic condensed hetero-aromatic rings each of which is formed by condensation of two of the monocyclic hetero-aromatic rings may be enumerated.

In the general formula (1), $X_1$-$X_4$ mutually independently represent hydrogen, linear- or branched-alkyl group having a carbon number of 1-18, cyclic alkyl group having a carbon number of 3-18, linear- or branched-alkenyl group having a carbon number of 2-18, cyclic alkenyl group having a carbon number of 3-18, aralkyl group having a carbon number of 7-20, aryl group having a carbon number of 6-18, halogen atom, nitro group, nitroso group, cyano group, isocyano group, cyanato group, isocyanato group, thiocyanato group, isothiocyanato group, mercapto group, hydroxy group, hydroxyamino group, formyl group, sulfo group, carboxyl group, acyl group, amino group, acylamino group, carbamate group, carboxylate group, acyloxy group, carbamoyl group, sulfonyl group, sulfamoyl group, sulfonate group, sulfonamide group, or sulfinyl group, wherein $X_2$ and $X_3$ may be optionally linked together to form a ring structure.

The following may be enumerated as the linear- or branched-alkyl group having a carbon number of 1-18, the cyclic alkyl group having a carbon number of 3-18, the linear- or branched-alkenyl group having a carbon number of 2-18, the cyclic alkenyl group having a carbon number of 3-18, the aralkyl group having a carbon number of 7-20, and the aryl group having a carbon number of 6-18, all of which can be used for $X_1$-$X_4$. Namely, as the linear- or branched-alkyl group having a carbon number of 1-18, for instance, methyl group, ethyl group, propyl group, isopropyl group, n-butyl group, sec-butyl group, tert-butyl group, n-heptyl group, etc., may be enumerated. As the cyclic alkyl group having a carbon number of 3-18, for instance, cyclopropyl group, cyclopentyl group, cyclohexyl group, adamantyl group, etc., may be enumerated. As the linear- or branched-alkenyl group having a carbon number of 2-18, for instance, vinyl group, propenyl group, hexenyl group, etc., may be enumarated. As the cyclic alkenyl group having a carbon number of 3-18, for instance, cyclopentenyl group, cyclohexenyl group, etc., may be enumerated. As the aralkyl group having a carbon number of 7-20, for instance, benzyl group, phenethyl group, etc., may be enumerated. As the aryl group having a carbon number of 6-18, for instance, phenyl group, tolyl group, xylyl group, mesityl group, etc., may be enumerated.

As the halogen atom which can be used for $X_1$-$X_4$, for instance, F, Cl, Br, and I may be enumerated.

The acyl group which can be used for $X_1$-$X_4$ is usually represented by —COR, the amino group which can be used ditto is usually represented by —NRR', the acylamino group which can be used ditto is usually represented by —NHCOR, the carbamate group c which can be used ditto is usually represented by —NHCOOR, the carboxylate group which can be used ditto is usually represented by —COOR, the acyloxy group which can be used ditto is usually represented by —OCOR, the carbamoyl group which can be used ditto is usually represented by —CONRR', the sulfonyl group which can be used ditto is usually represented by —$SO_2R$, the sulfamoyl group which can be used ditto is usually represented by —$SO_2NRR'$, the sulfone group which can be used ditto is usually represented by —$SO_2R$, the sulfonamide group which can be used ditto is usually represented by —$NHSO_2R$, and the sulfinyl group which can be used ditto is usually represented by —SOR. As for R, R', similar substituents which are described above may be used.

In the general formula (1), $X_2$ and $X_3$ may be optionally linked together to form a ring structure. Herein, the ring structure denotes that $X_2$ and $X_3$ exist as a cyclic substituent in which $X_2$ and $X_3$ share a part of their constitutive atoms. Concretely, $X_2$ and $X_3$ may be a cyclic alkyl group or aryl group having a carbon number of 3-18 which forms a 3- to 8-membered monocyclic ring, or a di- to tetra-cyclic condensed ring formed by condensation of the corresponding number of the monocyclic rings; or a hetero-aromatic group which forms a 5- to 6-membered monocyclic ring or a di- to tetra-cyclic condensed ring formed by condensation of the corresponding number of the monocyclic rings.

It is desirable that at least one of $Y_1$ and $Y_3$ in the general formula (1) is a substituent other than hydrogen. Thereby, it becomes possible to obtain an isoidole derivative, which may bring facility to the production of the stable product.

Preferable concrete examples of the above mentioned monomeric compound of which molecule includes one structure of bicyclopyrrole is shown below. In the following individual compounds, "Et" represents ethyl group, "Ph" represents phenyl group, and "TMS" represents trimethyl silyl group, respectively.

[Chemical 6]

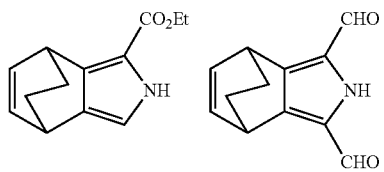

[Chemical 7]

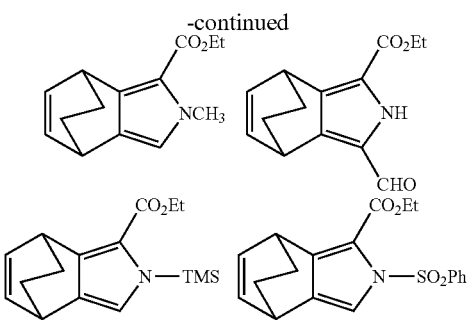

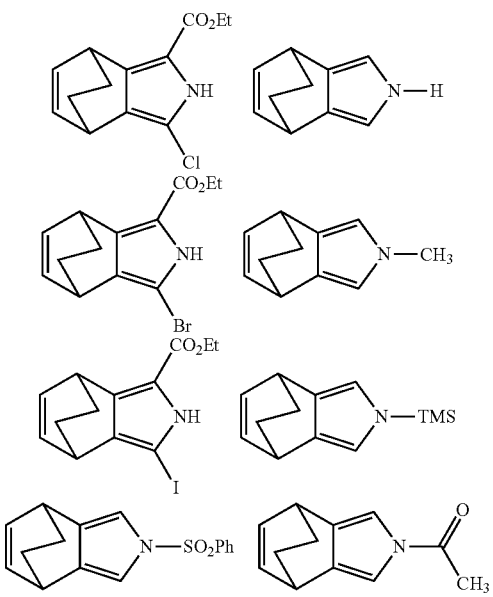

The monomeric compounds each of which molecule includes a structure of bicyclopyrrole as described above can be synthesized in accordance with the methods known in the art. As such methods, for instance, ones which are disclosed in J. Chem. Soc., Perkin Trans 1, 3661-3665, 1997 may be mentioned.

(Polymeric Compound of which Molecule Includes Two or More of Structures of Bicyclopyrroles)

When a polymeric compound of which molecule includes two or more of structures of bicyclopyrroles, i.e., the compound of which molecule includes two or more of the structures of pyrroles fused with bicyclo [2.2.2] octadiene skeletons, it is desirable to use the compound represented by the following general formula (2).

[Chemical 8]

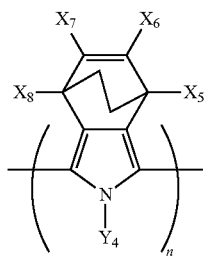

(2)

(In the general formula (2), n represents an integer of more than 1;

$Y_4$ represents hydrogen, linear- or branched-alkyl group having a carbon number of 1-18, cyclic alkyl group having a carbon number of 3-18, linear- or branched-alkenyl group having a carbon number of 2-18, cyclic alkenyl group having a carbon number of 3-18, aralkyl group having a carbon number of 7-20, aryl group having a carbon number of 6-18, formyl group, sulfo group, carboxyl group, acyl group, carboxylate group, acyloxy group, carbamoyl group, sulfonyl group, sulfamoyl group, silyl group, or heterocyclic group;

$X_5$-$X_8$ mutually independently represent hydrogen, linear- or branched-alkyl group having a carbon number of 1-18, cyclic alkyl group having a carbon number of 3-18, linear- or branched-alkenyl group having a carbon number of 2-18, cyclic alkenyl group having a carbon number of 3-18, aralkyl group having a carbon number of 7-20, aryl group having a carbon number of 6-18, halogen atom, nitro group, nitroso group, cyano group, isocyano group, cyanato group, isocyanato group, thiocyanate group, isothiocyanato group, mercapto group, hydroxy group, hydroxyamino group, formyl group, sulfo group, carboxyl group, acyl group, amino group, acylamino group, carbamate group, carboxylate group, acyloxy group, carbamoyl group, sulfonyl group, sulfamoyl group, sulfonate group, sulfonamide group, or sulfinyl group; wherein $X_6$ and $X_7$ may be optionally linked together to form a ring structure.)

When adopting the compounds represented by the general formula (2), it becomes possible to use various polymer compounds each of which molecule includes two or more of structures of bicyclopyrroles, and as a result, it becomes possible to obtain various polyisoindoles. Especially, although the polyisoindole is hardly obtained by the polymerization of isoindole (e.g., electrolytic polymerization), but it becomes easy to obtain the polyisoindole when using the manufacturing method of the present invention, since the polypyrrole which is fused with bicyclo [2.2.2] octadiene ring can be utilized therein. Further, the polyisoindole is expected to become a very useful novel material, because the polyisoindole has a high possibility of being a transparent electroconductive polymer.

In the general formula (2), n represents an integer of more than 1. Although n may be decided arbitrarily depending on the polymerization degree, it is preferable that n is not less than 15, and usually not more than 5000, desirably not more than 3000.

In the general formula (2), $Y_4$ represents hydrogen, linear- or branched-alkyl group having a carbon number of 1-18, cyclic alkyl group having a carbon number of 3-18, linear- or branched-alkenyl group having a carbon number of 2-18, cyclic alkenyl group having a carbon number of 3-18, aralkyl group having a carbon number of 7-20, aryl group having a carbon number of 6-18, formyl group, sulfo group, carboxyl group, acyl group, carboxylate group, acyloxy group, carbamoyl group, sulfonyl group, sulfamoyl group, silyl group, or heterocyclic group. Because $Y_4$ may be defined in a similar fashion to $Y_2$ in the general formula (1) as described above, the detailed explanation is omitted here to avoid the repetition of the explanation.

In the general formula (2), $X_5$-$X_8$ mutually independently represent hydrogen, linear- or branched-alkyl group having a carbon number of 1-18, cyclic alkyl group having a carbon number of 3-18, linear- or branched-alkenyl group having a carbon number of 2-18, cyclic alkenyl group having a carbon number of 3-18, aralkyl group having a carbon number of 7-20, aryl group having a carbon number of 6-18, halogen atom, nitro group, nitroso group, cyano group, isocyano group, cyanato group, isocyanato group, thiocyanato group, isothiocyanato group, mercapto group, hydroxy group, hydroxyamino group, formyl group, sulfo group, carboxyl group, acyl group, amino group, acylamino group, carbamate group, carboxylate group, acyloxy group, carbamoyl group, sulfonyl group, sulfamoyl group, sulfonate group, sulfonamide group, or sulfinyl group; wherein $X_6$ and $X_7$ may be optionally linked together to form a ring structure.

Because $X_5$-$X_8$ may be defined in a similar fashion to $X_1$-$X_4$ in the general formula (1) as described above, the detailed explanation is omitted here to avoid the repetition of the explanation. For instance, the meaning of "$X_6$ and $X_7$ may be optionally linked together to form a ring structure" is that $X_6$ and $X_7$ exist as a cyclic substituent in which $X_6$ and $X_7$ share a part of their constitutive atoms. Concretely, $X_6$ and $X_7$ may be a cyclic alkyl group or aryl group having a carbon number of 3-18 which forms a 3- to 8-membered monocyclic ring, or a di- to tetra-cyclic condensed ring formed by condensation of the corresponding number of the monocyclic rings; or a hetero-aromatic group which forms a 5- to 6-membered monocyclic ring or a di- to tetra-cyclic condensed ring formed by condensation of the corresponding number of the monocyclic rings.

The polymeric compounds each of which molecule includes two or more of structures of bicyclopyrroles as described above can be synthesized in accordance with the methods known in the art. As such methods, for instance, a method where the monomeric compound of which molecule includes a structure of bicyclopyrrole is obtained firstly, and then the monomeric compound undergoes the electrolytic polymerization may be enumerated.

With respect to the polymeric compound of which molecule includes two or more of structures of bicyclopyrroles, it is also desirable to use bicycloporphyrins represented by the following general formula (3A) or the following general formula (3B). The general formula (3A) indicates non-metal type bicycloporphyrins, and the general formula (3B) indicates bicycloporphyrins which have a central metal.

[Chemical 9]

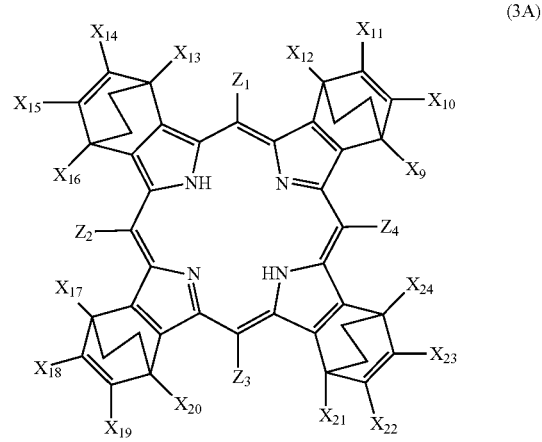

(3A)

-continued

[Chemical 10]

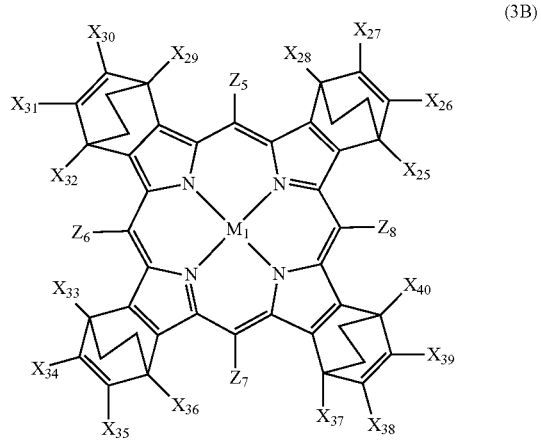

(3B)

(In the general formula (3A) and the general formula (3B), $Z_1$-$Z_3$ mutually independently represent hydrogen, linear- or branched-alkyl group having a carbon number of 1-18, cyclic alkyl group having a carbon number of 3-18, linear- or branched-alkenyl group having a carbon number of 2-18, cyclic alkenyl group having a carbon number of 3-18, aralkyl group having a carbon number of 7-20, aryl group having a carbon number of 6-18, halogen atom, nitro group, nitroso group, cyano group, isocyano group, cyanato group, isocyanato group, thiocyanato group, isothiocyanato group, mercapto group, hydroxy group, hydroxyamino group, formyl group, sulfo group, carboxyl group, acyl group, amino group, acylamino group, carbamate group, carboxylate group, acyloxy group, or carbamoyl group;

$X_9$-$X_{40}$ mutually independently represent hydrogen, linear- or branched-alkyl group having a carbon number of 1-18, cyclic alkyl group having a carbon number of 3-18, linear- or branched-alkenyl group having a carbon number of 2-18, cyclic alkenyl group having a carbon number of 3-18, aralkyl group having a carbon number of 7-20, aryl group having a carbon number of 6-18, halogen atom, nitro group, nitroso group, cyano group, isocyano group, cyanato group, isocyanato group, thiocyanato group, isothiocyanato group, mercapto group, hydroxy group, hydroxyamino group, formyl group, sulfo group, carboxyl group, acyl group, amino group, acylamino group, carbamate group, carboxylate group, acyloxy group, carbamoyl group, sulfonyl group, sulfamoyl group, sulfonate group, sulfonamide group, or sulfinyl group; wherein $X_{10}$ and $X_{11}$, $X_{14}$ and $X_{15}$, $X_{18}$ and $X_{19}$, $X_{22}$ and $X_{23}$, $X_{26}$ and $X_{27}$, $X_{30}$ and $X_{31}$, $X_{34}$ and $X_{35}$, and $X_{38}$ and $X_{39}$ may be optionally linked together, respectively, to form their individual ring structures; and $M_1$ represents a metal atom.)

When adopting the compounds represented by the general formula (3A) and the general formula (3B), it becomes possible to use a variety of bicycloporphyrins, and as a result, it becomes possible to obtain various tetrabenzoporphyrins. Especially, since the tetrabenzoporphyrin is a useful material which is used as organic semiconductor, photosensitizer for photo dynamic therapy of cancer, solar cell material, and pigment, etc., it is desirable to become easy to obtain the tetrabenzoporphyrin of high purity by using the manufacturing method according to the present invention.

In the general formula (3A) and the general formula (3B), $Z_1$-$Z_8$ mutually independently represent hydrogen, linear- or branched-alkyl group having a carbon number of 1-18, cyclic alkyl group having a carbon number of 3-18, linear- or branched-alkenyl group having a carbon number of 2-18, cyclic alkenyl group having a carbon number of 3-18, aralkyl group having a carbon number of 7-20, aryl group having a carbon number of 6-18, halogen atom, nitro group, nitroso group, cyano group, isocyano group, cyanato group, isocyanato group, thiocyanato group, isothiocyanato group, mercapto group, hydroxy group, hydroxyamino group, formyl group, sulfo group, carboxyl group, acyl group, amino group, acylamino group, carbamate group, carboxylate group, acyloxy group, or carbamoyl group.

The following may be enumerated as the linear- or branched-alkyl group having a carbon number of 1-18, the cyclic alkyl group having a carbon number of 3-18, the linear- or branched-alkenyl group having a carbon number of 2-18, the cyclic alkenyl group having a carbon number of 3-18, the aralkyl group having a carbon number of 7-20, and the aryl group having a carbon number of 6-18, all of which can be used for $Z_1$-$Z_8$. Namely, as the linear- or branched-alkyl group having a carbon number of 1-18, for instance, methyl group, ethyl group, propyl group, isopropyl group, n-butyl group, sec-butyl group, tert-butyl group, n-heptyl group, etc., may be enumerated. As the cyclic alkyl group having a carbon number of 3-18, for instance, cyclopropyl group, cyclopentyl group, cyclohexyl group, adamantyl group, etc., may be enumerated. As the linear- or branched-alkenyl group having a carbon number of 2-18, for instance, vinyl group, propenyl group, hexenyl group, etc., may be enumarated. As the cyclic alkenyl group having a carbon number of 3-18, for instance, cyclopentenyl group, cyclohexenyl group, etc., may be enumerated. As the aralkyl group having a carbon number of 7-20, for instance, benzyl group, phenethyl group, etc., may be enumerated. As the aryl group having a carbon number of 6-18, for instance, phenyl group, tolyl group, xylyl group, mesityl group, etc., may be enumerated.

As the halogen atom which can be used for $Z_1$-$Z_8$, for instance, F, Cl, Br, and I may be enumerated.

The acyl group which can be used for $Z_1$-$Z_8$ is usually represented by —COR, the amino group which can be used ditto is usually represented by —NRR', the acylamino group which can be used ditto is usually represented by —NHCOR, the carbamate group c which can be used ditto is usually represented by —NHCOOR, the carboxylate group which can be used ditto is usually represented by —COOR, the acyloxy group which can be used ditto is usually represented by —OCOR, and the carbamoyl group which can be used ditto is usually represented by —CONRR'. As for R, R', similar substituents which are described above with respect to the general formula (1) may be used.

In the general formula (3A) and the general formula (3B), $X_9$-$X_{40}$ mutually independently represent hydrogen, linear- or branched-alkyl group having a carbon number of 1-18, cyclic alkyl group having a carbon number of 3-18, linear- or branched-alkenyl group having a carbon number of 2-18, cyclic alkenyl group having a carbon number of 3-18, aralkyl group having a carbon number of 7-20, aryl group having a carbon number of 6-18, halogen atom, nitro group, nitroso group, cyano group, isocyano group, cyanato group, isocyanato group, thiocyanato group, isothiocyanato group, mercapto group, hydroxy group, hydroxyamino group, formyl group, sulfo group, carboxyl group, acyl group, amino group, acylamino group, carbamate group, carboxylate group, acyloxy group, carbamoyl group, sulfonyl group, sulfamoyl group, sulfonate group, sulfonamide group, or sulfinyl group; wherein $X_{10}$ and $X_{11}$, $X_{14}$ and $X_{15}$, $X_{18}$ and $X_{19}$, $X_{22}$ and $X_{23}$, $X_{26}$ and $X_{27}$, $X_{30}$ and $X_{31}$, $X_{34}$ and $X_{35}$, and $X_{38}$ and $X_{39}$ may be optionally linked together, respectively, to form their individual ring structures.

Because $X_9$-$X_{40}$ may be defined in a similar fashion to $X_1$-$X_4$ in the general formula (1) as described above, the detailed explanation is omitted here to avoid the repetition of the explanation. For instance, the meaning of "$X_{10}$ and $X_{11}$, $X_{14}$ and $X_{15}$, $X_{18}$ and $X_{19}$, $X_{22}$ and $X_{23}$, $X_{26}$ and $X_{27}$, $X_{30}$ and $X_{31}$, $X_{34}$ and $X_{35}$, and $X_{38}$ and $X_{39}$ may be optionally linked together, respectively, to form their individual ring structures" is that each individual pair of and $X_{10}$ and $X_{11}$, $X_{14}$ and $X_{15}$, $X_{18}$ and $X_{19}$, $X_{22}$ and $X_{23}$, $X_{26}$ and $X_{27}$, $X_{30}$ and $X_{31}$, $X_{34}$ and $X_{35}$, and $X_{38}$ and $X_{39}$ exist as a cyclic substituent in which the members of each pair share a part of their constitutive atoms. Concretely, each individual pair of $X_{10}$ and $X_{11}$, $X_{14}$ and $X_{15}$, $X_{18}$ and $X_{19}$, $X_{22}$ and $X_{23}$, $X_{26}$ and $X_{27}$, $X_{30}$ and $X_{31}$, $X_{34}$ and $X_{35}$, and $X_{38}$ and $X_{39}$ may be a cyclic alkyl group or aryl group having a carbon number of 3-18 which forms a 3- to 8-membered monocyclic ring, or a di- to tetra-cyclic condensed ring formed by condensation of the corresponding number of the monocyclic rings; or a hetero-aromatic group which forms a 5- to 6-membered monocyclic ring or a di- to tetra-cyclic condensed ring formed by condensation of the corresponding number of the monocyclic rings.

In the general formula (3B), $M_1$ represents a metal atom. Although the kind of the metal atom is not particularly limited, for instance, Cu, Zn, Ni, Pt, Pd, Mg, Cd, Mn, Fe, Co, Ti, Si, etc., may be enumerated.

The bicycloporphyrins as mentioned above can be synthesized in accordance with the methods known in the art. As such methods, for instance, the method disclosed in the above mentioned non-patent literature 3 may be enumerated.

With respect to the polymeric compound of which molecule includes two or more of structures of bicyclopyrroles, it is also desirable to use pyrromethenes represented by the following general formula (4).

[Chemical 11]

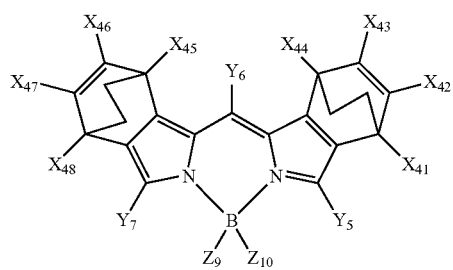

(4)

(In the general formula (4), $Y_5$ and $Y_7$ mutually independently represent hydrogen, linear- or branched-alkyl group having a carbon number of 1-18, cyclic alkyl group having a carbon number of 3-18, linear- or branched-alkenyl group having a carbon number of 2-18, cyclic alkenyl group having a carbon number of 3-18, aralkyl group having a carbon number of 7-20, aryl group having a carbon number of 6-18, halogen atom, nitro group, nitroso group, cyano group, isocyano group, cyanato group, isocyanato group, thiocyanato group, isothiocyanato group, mercapto group, hydroxy group, hydroxyamino group, formyl group, sulfo group, carboxyl group, acyl group, amino group, acylamino group, carbamate group, carboxylate group, acyloxy group, carbamoyl group, sulfonyl group, sulfamoyl group, sulfonate group, sulfonamide group, sulfinyl group or heterocyclic group;

$Y_6$ represents hydrogen, linear- or branched-alkyl group having a carbon number of 1-18, cyclic alkyl group having a carbon number of 3-18, linear- or branched-alkenyl group having a carbon number of 2-18, cyclic alkenyl group having a carbon number of 3-18, aralkyl group having a carbon number of 7-20, aryl group having a carbon number of 6-18, or heterocyclic group;

$Z_9$ and $Z_{10}$ mutually independently represent hydrogen, linear- or branched-alkyl group having a carbon number of 1-18, aryl group having a carbon number of 6-18, halogen atom, or a monovalent group of pyrrole fused with bicyclo [2.2.2] octadiene skeleton or derivative thereof;

$X_{41}$-$X_{48}$ mutually independently represent hydrogen, linear- or branched-alkyl group having a carbon number of 1-18, cyclic alkyl group having a carbon number of 3-18, linear- or branched-alkenyl group having a carbon number of 2-18, cyclic alkenyl group having a carbon number of 3-18, aralkyl group having a carbon number of 7-20, aryl group having a carbon number of 6-18, halogen atom, nitro group, nitroso group, cyano group, isocyano group, cyanato group, isocyanato group, thiocyanato group, isothiocyanato group, mercapto group, hydroxy group, hydroxyamino group, formyl group, sulfo group, carboxyl group, acyl group, amino group, acylamino group, carbamate group, carboxylate group, acyloxy group, carbamoyl group, sulfonyl group, sulfamoyl group, sulfonate group, sulfonamide group, or sulfinyl group; wherein $X_{42}$ and $X_{43}$, and $X_{46}$ and $X_{47}$ may be optionally linked together, respectively, to form their individual ring structures.)

When adapting the compounds represented by the general formula (4), it becomes possible to use a variety of pyrromethenes, and as a result, it becomes possible to obtain various benzopyrromethenes.

In the general formula (4), $Y_5$ and $Y_7$ mutually independently represent hydrogen, linear- or branched-alkyl group having a carbon number of 1-18, cyclic alkyl group having a carbon number of 3-18, linear- or branched-alkenyl group having a carbon number of 2-18, cyclic alkenyl group having a carbon number of 3-18, aralkyl group having a carbon number of 7-20, aryl group having a carbon number of 6-18, halogen atom, nitro group, nitroso group, cyano group, isocyano group, cyanato group, isocyanato group, thiocyanato group, isothiocyanato group, mercapto group, hydroxy group, hydroxyamino group, formyl group, sulfo group, carboxyl group, acyl group, amino group, acylamino group, carbamate group, carboxylate group, acyloxy group, carbamoyl group, sulfonyl group, sulfamoyl group, sulfonate group, sulfonamide group, sulfinyl group or heterocyclic group.

The following may be enumerated as the linear- or branched-alkyl group having a carbon number of 1-18, the cyclic alkyl group having a carbon number of 3-18, the linear- or branched-alkenyl group having a carbon number of 2-18, the cyclic alkenyl group having a carbon number of 3-18, the aralkyl group having a carbon number of 7-20, and the aryl group having a carbon number of 6-18, all of which can be used for $Y_5$ and $Y_7$. Namely, as the linear- or branched-alkyl group having a carbon number of 1-18, for instance, methyl group, ethyl group, propyl group, isopropyl group, n-butyl group, sec-butyl group, tert-butyl group, n-heptyl group, etc., may be enumerated. As the cyclic alkyl group having a carbon number of 3-18, for instance, cyclopropyl group, cyclopentyl group, cyclohexyl group, adamantyl group, etc., may be enumerated. As the linear- or branched-alkenyl group having a carbon number of 2-18, for instance, vinyl group, propenyl group, hexenyl group, etc. may be enumarated. As the cyclic alkenyl group having a carbon number of 3-18, for instance, cyclopentenyl group, cyclohexenyl group, etc., may be enumerated. As the aralkyl group having a carbon number of 7-20, for instance, benzyl group, phenethyl group, etc., may be enumerated. As the aryl group having a carbon number of 6-18, for instance, phenyl group, tolyl group, xylyl group, mesityl group, etc., may be enumerated.

As the halogen atom which can be used for $Y_5$ and $Y_7$ for instance, F, Cl, Br, and I may be enumerated.

The acyl group which can be used for $Y_5$ and $Y_7$ is usually represented by —COR, the amino group which can be used ditto is usually represented by —NRR', the acylamino group which can be used ditto is usually represented by —NHCOR, the carbamate group c which can be used ditto is usually represented by —NHCOOR, the carboxylate group which can be used ditto is usually represented by —COOR, the acyloxy group which can be used ditto is usually represented by —OCOR, the carbamoyl group which can be used ditto is usually represented by —CONRR', the sulfonyl group which can be used ditto is usually represented by —SO$_2$R, the sulfamoyl group which can be used ditto is usually represented by —SO$_2$NRR', the sulfonate group which can be used ditto is usually represented by —SO$_3$R, the sulfonamide group which can be used ditto is usually represented by —NHSO$_2$R, and the sulfinyl group which can be used ditto is usually represented by —SOR. As for R, R', similar substituents which are described above with respect to the general formula (1) may be used.

With respect to the heterocyclic group which can be used for $Y_5$ and $Y_7$, it may be either a saturated heterocyclic group, such as 4-piperidyl group, morpholino group, 2-morpholinyl group, piperazyl groups, etc; or a aromatic heterocyclic group, such as 2-furyl group, 2-pyridyl group, 2-thiazolyl group, 2-quinolyl group, etc. The heterocyclic group may contain two or more number of heteroatoms, and may have additional substituent(s), optionally. Further, there is no particular limitation for the binding site thereof. As preferable structures for the heterocyclic ring, 5- and 6-membered saturated heterocyclic rings, 5- and 6-membered monocyclic hetero-aromatic rings, and dicyclic condensed hetero-aromatic rings each of which is formed by condensation of two of the monocyclic hetero-aromatic rings may be enumerated.

In the general formula (4), $Y_6$ represents hydrogen, linear- or branched-alkyl group having a carbon number of 1-18, cyclic alkyl group having a carbon number of 3-18, linear- or branched-alkenyl group having a carbon number of 2-18, cyclic alkenyl group having a carbon number of 3-18, aralkyl group having a carbon number of 7-20, aryl group having a carbon number of 6-18, or heterocyclic group.

The following may be enumerated as the linear- or branched-alkyl group having a carbon number of 1-18, the cyclic alkyl group having a carbon number of 3-18, the linear- or branched-alkenyl group having a carbon number of 2-18, the cyclic alkenyl group having a carbon number of 3-18, the aralkyl group having a carbon number of 7-20, and the aryl group having a carbon number of 6-18, all of which can be used for $Y_6$. Namely, as the linear- or branched-alkyl group having a carbon number of 1-18, for instance, methyl group, ethyl group, propyl group, isopropyl group, n-butyl group, sec-butyl group, tert-butyl group, n-heptyl group, etc., may be enumerated. As the cyclic alkyl group having a carbon number of 3-18, for instance, cyclopropyl group, cyclopentyl group, cyclohexyl group, adamantyl group, etc., may be enumerated. As the linear- or branched-alkenyl group having a carbon number of 2-18, for instance, vinyl group, propenyl group, hexenyl group, etc., may be enumerated. As the cyclic alkenyl group having a carbon number of 3-18, for instance, cyclopentenyl group, cyclohexenyl group, etc., may be enumerated. As the aralkyl group having a carbon number of 7-20, for instance, benzyl group, phenethyl group, etc., may be enumerated. As the aryl group having a carbon number of 6-18, for instance, phenyl group, tolyl group, xylyl group, mesityl group, etc., may be enumerated.

With respect to the heterocyclic group which can be used for $Y_6$, it may be either a saturated heterocyclic group, such as 4-piperidyl group, morpholino group, 2-morpholinyl group, piperazyl groups, etc; or a aromatic heterocyclic group, such as 2-furyl group, 2-pyridyl group, 2-thiazolyl group, 2-quinolyl group, etc. The heterocyclic group may contain two or more number of heteroatoms, and may have additional substituent(s), optionally. Further, there is no particular limitation for the binding site thereof. As preferable structures for the heterocyclic ring, 5- and 6-membered saturated heterocyclic rings, 5- and 6-membered monocyclic hetero-aromatic rings, and dicyclic condensed hetero-aromatic rings each of which is formed by condensation of two of the monocyclic hetero-aromatic rings may be enumerated.

In the general formula (4), $Z_9$ and $Z_{10}$ mutually independently represent hydrogen, linear- or branched-alkyl group having a carbon number of 1-18, aryl group having a carbon number of 6-18, halogen atom, or a monovalent group of pyrrole fused with bicyclo [2.2.2] octadiene skeleton or derivative thereof.

As the linear- or branched-alkyl group having a carbon number of 1-18, which can be used for $Z_9$ and $Z_{10}$, for instance, methyl group, ethyl group, propyl group, isopropyl group, n-butyl group, sec-butyl group, tert-butyl group, n-heptyl group, etc., may be enumerated. As the aryl group having a carbon number of 6-18, which can be used for $Z_9$ and $Z_{10}$, for instance, phenyl group, tolyl group, xylyl group, mesityl group, etc., may be enumerated.

As the halogen atom which can be used for $Z_9$ and $Z_{10}$, for instance, F, Cl, Br, and I may be enumerated.

As the monovalent group of pyrrole fused with bicyclo [2.2.2] octadiene skeleton or derivative thereof, which can be used for $Z_9$ and $Z_{10}$, for instance, a monovalent substituent which is formed by eliminating $Y_2$ from the compound described by the general formula (1) may be enumerated.

In the general formula (4), $X_{41}$-$X_{48}$ mutually independently represent hydrogen, linear- or branched-alkyl group having a carbon number of 1-18, cyclic alkyl group having a carbon number of 3-18, linear- or branched-alkenyl group having a carbon number of 2-18, cyclic alkenyl group having a carbon number of 3-18, aralkyl group having a carbon number of 7-20, aryl group having a carbon number of 6-18, halogen atom, nitro group, nitroso group, cyano group, isocyano group, cyanato group, isocyanato group, thiocyanato group, isothiocyanato group, mercapto group, hydroxy group, hydroxyamino group, formyl group, sulfo group, carboxyl group, acyl group, amino group, acylamino group, carbamate group, carboxylate group, acyloxy group, carbamoyl group, sulfonyl group, sulfamoyl group, sulfonate group, sulfonamide group, or sulfinyl group; wherein $X_{42}$ and $X_{43}$, and $X_{46}$ and $X_{47}$ may be optionally linked together, respectively, to form their individual ring structures.

Because $X_{41}$-$X_{48}$ may be defined in a similar fashion to $X_1$-$X_4$ in the general formula (1) as described above, the detailed explanation is omitted here to avoid the repetition of the explanation. For instance, the meaning of "$X_{42}$ and $X_{43}$, and $X_{46}$ and $X_{47}$ may be optionally linked together, respectively, to form their individual ring structures" is that each individual pair of $X_{42}$ and $X_{43}$, and $X_{46}$ and $X_{47}$ exist as a cyclic substituent in which the members of each pair share a part of their constitutive atoms. Concretely, each individual pair of $X_{42}$ and $X_{43}$, and $X_{46}$ and $X_{47}$ may be a cyclic alkyl group or aryl group having a carbon number of 3-18 which forms a 3- to 8-membered monocyclic ring, or a di- to tetra-cyclic condensed ring formed by condensation of the corresponding number of the monocyclic rings; or a hetero-aromatic group which forms a 5- to 6-membered monocyclic ring or a di- to tetra-cyclic condensed ring formed by condensation of the corresponding number of the monocyclic rings.

The pyrromethenes as mentioned above can be synthesized in accordance with the methods known in the art. As such methods, for instance, the method disclosed in M. Wada, S. Ito, H. Uno, T. Murashima, N. Ono, T. Urano and Y. Urano, Tetrahedron Lett., 42, 6711-6713 (2001).

(Thermal Treatment)

The compound of which molecule includes the structure of pyrrole fused with bicyclo [2.2.2] octadiene skeleton is subjected to a supercritical carbon dioxide atmosphere.

The compound of which molecule includes the structure of bicyclopyrrole is subjected to the supercritical carbon dioxide atmosphere. By using the supercritical carbon dioxide atmosphere, it becomes easy to disperse the compound of which molecule includes the structure of bicyclopyrrole within the reaction system, and further, it becomes possible to solve it in the reaction system. As a consequence, it becomes easy to transmit heat to the compound of which molecule includes the structure of bicyclopyrrole effectively, and which fact contributes to improvement tendency of reaction efficiency. Herein, the "supercritical carbon dioxide" refers to carbon dioxide which is brought in a state which shows properties both of gas and liquid, by setting carbon dioxide to a condition higher than its critical temperature (31° C.) and critical pressure (7.4 MPa). At the temperature higher than the critical temperature, however, the carbon dioxide can not condense even if it is compressed. Thus, the carbon dioxide which is in a condition higher than its critical temperature may be called the supercritical carbon dioxide, regardless of its pressure condition. The present invention can enjoys the excellent characteristics owned by the supercritical carbon dioxide, such as reaction controllability and separation capability, etc., since the reaction of the present invention can progress even in the supercritical carbon dioxide.

With respect to the pressure of the atmosphere, it may be set, usually, not less than 0.1 MPa, and usually, not more than 50 MPa, desirably, not more than 30 MPa. When adopting the pressure of the above range, it becomes possible to make the carbon dioxide to the supercritical carbon dioxide even at a relatively low pressure condition including the supercritical range of pressure, by raising the temperature.

Further, with respect to the purity of the atmosphere, although there is no particular limitation, the purity is usually set to 99.995% or more. The higher purity becomes, the more it is desirable. However, because it is not easy to exclude impurities completely industrially, the purity will usually fall in the above mentioned range. Although it is in the "supercritical carbon dioxide atmosphere", the atmosphere usually contains impurities in a constant amount as described above from an industrial viewpoint. Therefore, there is a certain possibility of generating any compound other than the intended isoindolic compound, due to the reaction of the compound of which molecule includes the structure of bicyclopyrrole with such impurities. Such a reaction would be allowed within the scope and spirit of the present invention.

The thermal treatment step is preferably performed at a temperature of not less than 50° C. and not more than 300° C. Thereby, the thermal treatment in a desirable range of the temperature is accomplished. As a result, it is possible to produce the isoindolic compound more efficiently. Although the temperature at the thermal treatment would determine the reaction temperature, the method for manufacturing isoindolic compound according to the present invention can greatly decrease the reaction temperature as compared with those in the conventional methods. The reaction temperature is preferably set to be not more than 270° C., more preferably, not more than 250° C., and further more preferably, not more than 240° C. In addition, the reaction temperature is preferably set to be not less than 80° C. Thereby, it becomes possible to progress the reaction at lower temperature. As a result, the manufacturing method of the present invention would be evaluated as a more industrially adaptable manufacturing method of the isoindolic compound.

The retaining time (reaction time) for subjecting the compound of which molecule includes the structure of bicyclopyrrole under the supercritical carbon dioxide atmosphere may be set usually to be not less than one minute, preferably, not less than 10 minutes, and usually to be not more than 300 minutes, preferably, not more than 120 minutes. When adapting the time within the above mentioned range, it becomes easy to progress certainly the reaction to the isoindolic compound.

Since the compound of which molecule includes the structure of bicyclopyrrole is subjected to the supercritical carbon dioxide atmosphere, and thereby, the reaction of converting bicyclo ring structure into benzene ring structure is motivated according to the manufacturing method of isoindolic compound of the present invention, there is an advantage of needlessness for addition of solvent or catalyst during the reaction. Thus, the manufacturing method of the present invention is the one which is simple, high speed, and high economical, and has a lowered load against the environment. Therefore, upon the reaction, it is not necessary to exist any component such as additive agent other than the compound of which molecule includes the structure of bicyclopyrrole in the reaction system. However, within the scope and spirit of the present invention, it would be possible to add a certain necessitated component at an appropriate amount upon the reaction.

(Other Steps)

In the method for manufacturing isoindolic compound according to the present invention, a certain necessitated previous step, such as a step for preparing the compound of which molecule includes the structure of bicyclopyrrole, may be provided appropriately in advance of the reaction step. As for such a preparing step, it is as explaining in the section of the above mentioned individual compounds.

In addition, as described above, the method for manufacturing isoindolic compound according to the present invention has the advantage of needlessness for addition of solvent or catalyst during the reaction. Therefore, a step for separating the product from the solvent and catalyst after the reaction can be omitted. Thus, the method for manufacturing isoindolic compound according to the present invention has an advantage that no post-step after the thermal treatment step is necessary. However, any prescribed post-step may be provided if necessary. As such a post-step, for instance, a step of removing impurities and the like which remain in the product in order to bring the purity of the isoindolic compound close to 100% may be enumerated.

(Isoindolic Compound)

The isoindolic compound of the present invention is the one manufactured from the above mentioned method for manufacturing isoindolic compound. Therefore, it is possible to provide the isoindolic compound which is obtained by the method for manufacturing isoindolic compound where the deairation in the reaction system can be progressed satisfactorily by means of the supercritical carbon dioxide atmosphere, and the compound of which molecule includes a structure of pyrrole fused with bicyclo [2.2.2] octadiene skeleton as a raw material can be dispersed and/or solved satisfactorily, which is followed by the implementation of an efficient thermal treatment, and thus the progress of the reaction at a relatively low temperature, the capability of applying a condition capable of being put to industrially practical use, the ability of producing stable isoindolic compound, and the ability of producing the isoindolic compound with a high yield.

The isoindolic compound of the present invention denotes the compound of which molecule contains one or more of isoindole structure(s). Since the compound of which molecule includes one or more of structure(s) of pyrrole(s) fused with bicyclo [2.2.2] octadiene skeleton(s) is used as a raw material, and then the bicyclo ring structure part(s) of the above mentioned compound is made to convert to the benzene ring structure(s), the obtained isoindolic compound comes to contain the isoindole structure(s) in its molecule. As the isoindolic compound, for instance, isoindole, isoindole derivatives, and polymeric compounds of isoindole, etc., may be enumerated. As the polymeric compounds of isoindole, for instance, polyisoindoles, pyrromethenes, tetrabenzoporphyrins, phthalocyanines may be enumerated. For the sake of the stability, it is preferable that the isoindolic compound is formed as isoindole derivative, or polymeric compound of isoindole.

EXAMPLE

Next, this invention will be described in detail with referring to examples. It should be understood, however, that the present invention is not limited to the description of the following examples, and the present invention can be practiced any mode as far as it belongs in the scope and spirit of the present invention.

Example 1

0.050 g of the compound shown below (ethyl 4,7-dihydro-4,7-ethano-2H-isoindole-1-carboxylate) was added into a reaction chamber having an inner volume of 50 ml and made of stainless steel.

[Chemical 12]

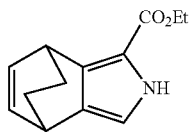

After adjusting the supercritical carbon dioxide in the reaction chamber to 20 MPa, the thermal treatment step were performed to react for 60 minutes while heating and stirring at 180° C. After the reaction, the reaction chamber were soaked into a cold water bath until the reaction chamber was cooled to a temperature in the vicinity of the room temperature, and then gas was emitted through a back pressure valve.

Then, the reaction chamber was opened, and the product was taken out. The product obtained was analyzed by nuclear magnetic resonance spectroscopy ($^1$HNMR) to identify the product. The nuclear magnetic resonance spectroscopy was performed by using VNMR500 manufactured by Varian company, and the determination condition was the condition in $CDCl_3$. As a result, it was found that ethyl 2H-isoindole-1-carboxylate which was the target material was obtained in crystal condition, and thus, it was able to be confirmed that the following reaction proceeded satisfyingly. The data of $^1$HNMR is shown below.

$^1$H NMR (500 MHz) δ 1.46 (t, 3H), 4.46 (q, 2H), 7.10 (m, 1H), 7.27 (m, 1H), 7.48 (m, 1H), 7.68 (m, 1H), 8.08 (m, 1H), 10.51 (brs, 1H).

[Chemical 13]

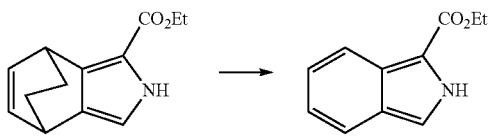

Example 2

0.050 g of the compound shown below (ethyl 3-chloro-4,7-dihydro-4,7-ethano-2H-isoindole-1-carboxylate) was added into a reaction chamber having an inner volume of 50 ml and made of stainless steel.

[Chemical 14]

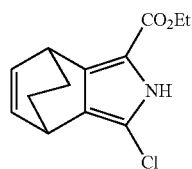

After adjusting the supercritical carbon dioxide in the reaction chamber to 20 MPa, the thermal treatment step were performed to react for 60 minutes while heating and stirring at 180° C. After the reaction, the reaction chamber were soaked into a cold water bath until the reaction chamber was cooled to a temperature in the vicinity of the room temperature, and then gas was emitted through a back pressure valve.

Then, the reaction chamber was opened, and the product was taken out. The product obtained was analyzed by nuclear magnetic resonance spectroscopy ($^1$HNMR) in an analogous fashion with Example 1 to identify the product. As a result, it was found that ethyl 3-chloro-2H-isoindole-1-carboxylate which was the target material was obtained in crystal condition, and thus, it was able to be confirmed that the following reaction proceeded satisfyingly. The data of $^1$HNMR is shown below.

$^1$H NMR (500 MHz) δ 1.45 (t, 3H), 4.43 (q, 2H), 7.15 (m, 1H), 7.28 (m, 1H), 7.57 (m, 1H), 8.01 (m, 1H), 10.14 (brs, 1H).

[Chemical 15]

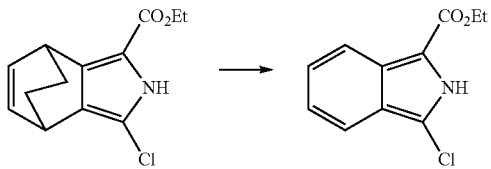

Example 3

0.050 g of the compound shown below (bicycloporphyrin) was added into a reaction chamber having an inner volume of 50 ml and made of stainless steel.

[Chemical 16]

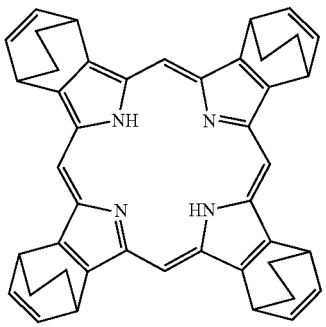

After adjusting the supercritical carbon dioxide in the reaction chamber to 20 MPa, the thermal treatment step were performed to react for 15 minutes while heating and stirring at 200° C. After the reaction, the reaction chamber were soaked into a cold water bath until the reaction chamber was cooled to a temperature in the vicinity of the room temperature, and then gas was emitted through a back pressure valve.

Then, the reaction chamber was opened, and the product was taken out. The product obtained was analyzed by ultraviolet visible absorption spectroscopy and mass spectrometry to identify the product. The ultraviolet visible absorption spectroscopy was performed by using V-630 manufactured by JASCO Corporation, and the determination condition was the condition in chloroform containing 5% trifluoroacetic acid. The mass spectrometry was performed by using a time-of-flight mass spectrometer (Autoflex-II) manufactured by Bruker corporation, and Dithranol as a matrix agent. As a result, it was found that tetrabenzoporphyrin which was the target material was obtained as green powder, and thus, it was able to be confirmed that the following reaction proceeded satisfyingly. The data of the ultraviolet visible absorption spectroscopy and the data of the mass spectrometry are shown below.

UV-vis (5% TFA-CHCl$_3$) $\lambda_{max}$ 431, 605, 660 nm; m/z (MALDI-TOF) 510 (M$^+$).

[Chemical 17]

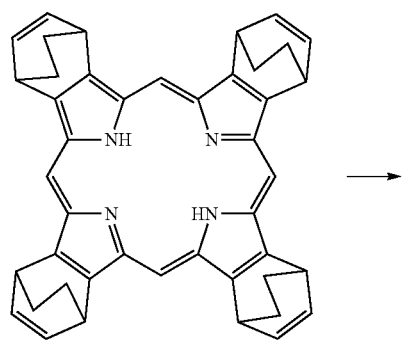

→

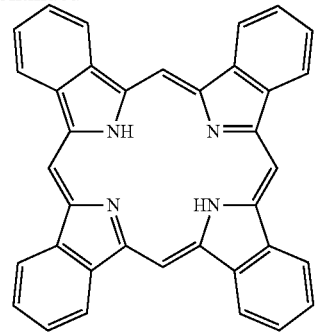

Example 4

0.050 g of the compound shown below (5,10,15,20-tetraphenyl bicycloporphyrin) was added into a reaction chamber having an inner volume of 50 ml and made of stainless steel. Incidentally, the "Ph" in the following chemical formula denotes phenyl group.

[Chemical 18]

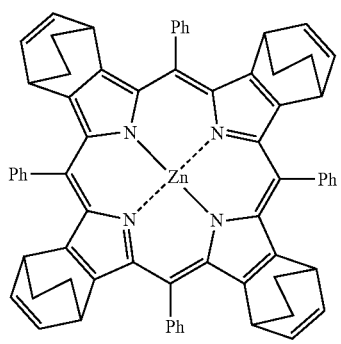

After adjusting the supercritical carbon dioxide in the reaction chamber to 20 MPa, the thermal treatment step were performed to react for 15 minutes while heating and stirring at 200° C. After the reaction, the reaction chamber were soaked into a cold water bath until the reaction chamber was cooled to a temperature in the vicinity of the room temperature, and then gas was emitted through a back pressure valve.

Then, the reaction chamber was opened, and the product was taken out. The product obtained was analyzed by ultraviolet visible absorption spectroscopy and mass spectrometry in an analogous fashion with Example 3 to identify the product. As a result, it was found that 5,10,15,20-tetraphenyl tetrabenzoporphyrin which was the target material was obtained as green powder, and thus, it was able to be confirmed that the following reaction proceeded satisfyingly. The data of the ultraviolet visible absorption spectroscopy and the data of the mass spectrometry are shown below.

UV-vis (CHCl$_3$) $\lambda_{max}$ 463, 609, 652 nm; m/z (MALDI-TOF) 875 (M$^+$).

[Chemical 19]

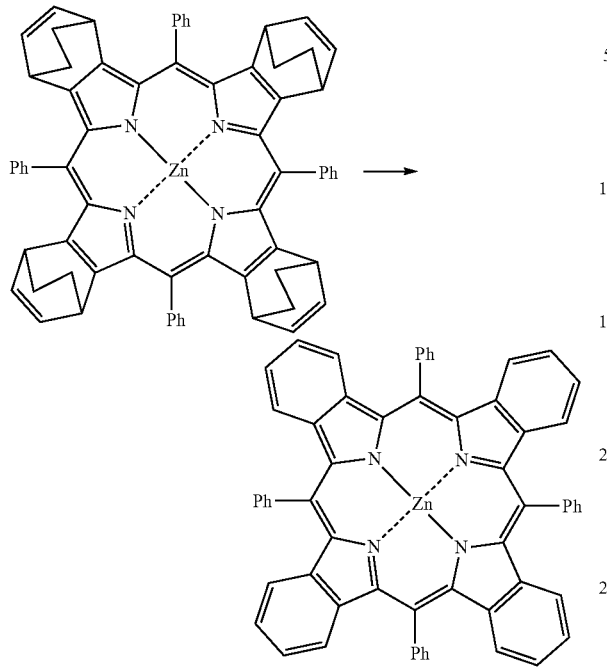

Example 5

0.050 g of the compound shown below (pyrromethene fused with bicyclo [2.2.2] octadiene ring) was added into a reaction chamber having an inner volume of 50 ml and made of stainless steel. Incidentally, the "Et" in the following chemical formula denotes ethyl group.

[Chemical 20]

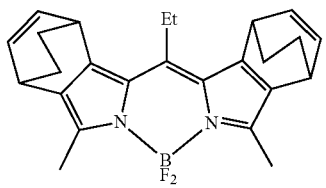

After adjusting the supercritical carbon dioxide in the reaction chamber to 20 MPa, the thermal treatment step were performed to react for 15 minutes while heating and stirring at 200° C. After the reaction, the reaction chamber were soaked into a cold water bath until the reaction chamber was cooled to a temperature in the vicinity of the room temperature, and then gas was emitted through a back pressure valve.

Then, the reaction chamber was opened, and the product was taken out. The product obtained was analyzed by nuclear magnetic resonance spectroscopy ($^1$HNMR) in an analogous fashion with Example 1 to identify the product. As a result, it was found that dibenzo pyrromethene which was the target material was obtained as gold powder, and thus, it was able to be confirmed that the following reaction proceeded satisfyingly. The data of $^1$HNMR is shown below.

$^1$NMR (CDCl$_3$), δ 1.57 (t, 3H), 2.93 (s, 6H), 3.49 (q, 2H), 7.25 (m, 2H), 7.42 (m, 2H), 7.73 (m, 2H), 7.89 (m, 2H).

[Chemical 21]

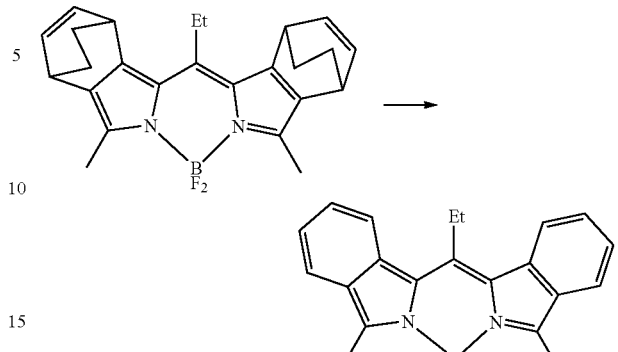

The invention claimed is:

1. A method for manufacturing isoindolic compound which comprises a thermal treatment step where a compound of which molecule includes a structure of pyrrole fused with bicyclo [2.2.2] octadiene skeleton is subjected to a supercritical carbon dioxide atmosphere,
wherein the compound of which molecule includes the structure of pyrrole fused with bicyclo [2.2.2] octadiene skeleton is represented by the following general formula (1):

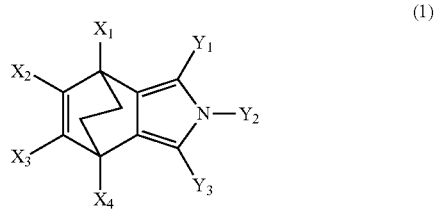

(1)

where in the general formula (1),
$Y_1$ and $Y_3$ mutually independently represent hydrogen, linear- or branched-alkyl group having a carbon number of 1-18, cyclic alkyl group having a carbon number of 3-18, linear- or branched-alkenyl group having a carbon number of 2-18, cyclic alkenyl group having a carbon number of 3-18, aralkyl group having a carbon number of 7-20, aryl group having a carbon number of 6-18, halogen atom, nitro group, nitroso group, cyano group, isocyano group, cyanato group, isocyanato group, thiocyanato group, isothiocyanato group, mercapto group, hydroxy group, hydroxyamino group, formyl group, sulfo group, carboxyl group, acyl group, amino group, acylamino group, carbamate group, carboxylate group, acyloxy group, carbamoyl group, sulfonyl group, sulfamoyl group, sulfonate group, sulfonamide group, sulfinyl group, or heterocyclic group;

$Y_2$ represents hydrogen, linear- or branched-alkyl group having a carbon number of 1-18, cyclic alkyl group having a carbon number of 3-18, linear- or branched-alkenyl group having a carbon number of 2-18, cyclic alkenyl group having a carbon number of 3-18, aralkyl group having a carbon number of 7-20, aryl group having a carbon number of 6-18, formyl group, sulfo group, carboxyl group, acyl group, carboxylate group, acyloxy group, carbamoyl group, sulfonyl group, sulfamoyl group, silyl group, or heterocyclic group; and $X_1$-$X_4$ mutually independently represent hydrogen, linear- or branched-alkyl group having a carbon number of 1-18, cyclic alkyl group having a carbon number of 3-18, linear- or branched-alkenyl group having a carbon number of 2-18, cyclic alkenyl group having a carbon number of 3-18, aralkyl group having a carbon number of 7-20, aryl group having a carbon number of 6-18, halogen atom, nitro group, nitroso group, cyano group, isocyano group, cyanato group, isocyanato group, thiocyanato group, isothiocyanato group, mercapto group, hydroxy group, hydroxyamino group, formyl group, sulfo group, carboxyl group, acyl group, amino group, acylamino group, carbamate group, carboxylate group, acyloxy group, carbamoyl group, sulfonyl group, sulfamoyl group, sulfonate group, sulfonamide group, or sulfinyl group; wherein $X_2$ and $X_3$ may be optionally linked together to form a ring structure.

2. The method for manufacturing isoindolic compound according to claim 1, wherein the thermal treatment step is performed at a temperature of not less than 50° C. and not more than 300° C., wherein the compound of which molecule includes the structure of pyrrole fused with bicyclo [2.2.2] octadiene skeleton is represented by the following general formula (5):

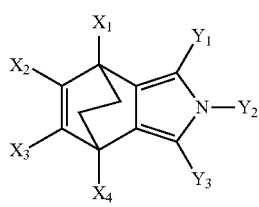

(5)

wherein in the general formula (5), $Y_1$ and $Y_3$ mutually independently represent hydrogen, linear- or branched-alkyl group having a carbon number of 1-18, cyclic alkyl group having a carbon number of 3-18, linear- or branched-alkenyl group having a carbon number of 2-18, cyclic alkenyl group having a carbon number of 3-18, aralkyl group having a carbon number of 7-20, aryl group having a carbon number of 6-18, halogen atom, nitro group, nitroso group, cyano group, isocyano group, cyanato group, isocyanato group, thiocyanato group, isothiocyanato group, mercapto group, hydroxy group, hydroxyamino group, formyl group, sulfo group, carboxyl group, acyl group, amino group, acylamino group, carbamate group, carboxylate group, acyloxy group, carbamoyl group, sulfonyl group, sulfamoyl group, sulfonate group, sulfonamide group, sulfinyl group, or heterocyclic group;

$Y_2$ represents hydrogen, linear- or branched-alkyl group having a carbon number of 1-18, cyclic alkyl group having a carbon number of 3-18, linear- or branched-alkenyl group having a carbon number of 2-18, cyclic alkenyl group having a carbon number of 3-18, aralkyl group having a carbon number of 7-20, aryl group having a carbon number of 6-18, formyl group, sulfo group, carboxyl group, acyl group, carboxylate group, acyloxy group, carbamoyl group, sulfonyl group, sulfamoyl group, silyl group, or heterocyclic group; and $X_1$-$X_4$ mutually independently represent hydrogen, linear- or branched-alkyl group having a carbon number of 1-18, cyclic alkyl group having a carbon number of 3-18, linear- or branched-alkenyl group having a carbon number of 2-18, cyclic alkenyl group having a carbon number of 3-18, aralkyl group having a carbon number of 7-20, aryl group having a carbon number of 6-18, halogen atom, nitro group, nitroso group, cyano group, isocyano group, cyanato group, isocyanato group, thiocyanato group, isothiocyanato group, mercapto group, hydroxy group, hydroxyamino group, formyl group, sulfo group, carboxyl group, acyl group, amino group, acylamino group, carbamate group, carboxylate group, acyloxy group, carbamoyl group, sulfonyl group, sulfamoyl group, sulfonate group, sulfonamide group, or sulfinyl group; wherein $X_2$ and $X_3$ may be optionally linked together to form a ring structure.

* * * * *